United States Patent [19]

Vu et al.

[11] Patent Number: 5,798,094
[45] Date of Patent: Aug. 25, 1998

[54] CLEAR COSMETIC STICK COMPOSITION WITH ALKALI CHELATE

[75] Inventors: Tuan M. Vu, Allston; Jayant N. Sane, Framingham; Craig M. Coe, Buzzards Bay, all of Mass.

[73] Assignee: The Gillette Company, Boston, Mass.

[21] Appl. No.: 718,884

[22] Filed: Sep. 24, 1996

[51] Int. Cl.$^6$ .................................................. A61K 7/32
[52] U.S. Cl. .................................................. 424/65
[58] Field of Search .................................. 424/65, 66, 67, 424/68

[56] References Cited

U.S. PATENT DOCUMENTS

| | | | |
|---|---|---|---|
| 4,226,889 | 10/1980 | Yuhas | 424/59 |
| 4,268,498 | 5/1981 | Gedeon et al. | 424/59 |
| 4,322,400 | 3/1982 | Yuhas | 424/59 |
| 4,440,742 | 4/1984 | Marschner | 424/65 |
| 4,478,821 | 10/1984 | Carrillo | 424/DIG. 5 |
| 4,504,465 | 3/1985 | Sampson et al. | 424/65 |
| 4,617,185 | 10/1986 | DiPietro | 424/65 |
| 4,759,924 | 7/1988 | Luebbe et al. | 424/65 |
| 4,906,454 | 3/1990 | Melanson et al. | 424/65 |
| 5,114,717 | 5/1992 | Kuznitz et al. | 424/65 |
| 5,120,541 | 6/1992 | Macaulay et al. | 424/59 |
| 5,128,123 | 7/1992 | Brewster et al. | 424/65 |
| 5,221,529 | 6/1993 | Tansley | 424/65 |
| 5,271,934 | 12/1993 | Goldberg et al. | 424/66 |
| 5,368,848 | 11/1994 | Brazinsky et al. | 424/65 |
| 5,407,668 | 4/1995 | Kellner | 424/65 |
| 5,424,070 | 6/1995 | Kasat et al. | 424/65 |
| 5,443,821 | 8/1995 | Smith et al. | 424/65 |
| 5,458,880 | 10/1995 | Kasat et al. | 424/65 |
| 5,462,736 | 10/1995 | Rech et al. | 424/65 |
| 5,552,136 | 9/1996 | Motley | 424/68 |
| 5,585,092 | 12/1996 | Trandai et al. | 424/65 |
| 5,597,556 | 1/1997 | Moghe et al. | 424/65 |
| 5,605,681 | 2/1997 | Trandai et al. | 424/65 |

FOREIGN PATENT DOCUMENTS

| | | |
|---|---|---|
| 089120 | 9/1983 | European Pat. Off. . |
| 284765 | 10/1988 | European Pat. Off. . |
| 521579 | 1/1993 | European Pat. Off. . |
| 0561489 | 9/1993 | European Pat. Off. . |

OTHER PUBLICATIONS

M. de Nevarre, The Chemistry and Manufacture of Cosmetics, vol. IV, p. 697 (1975).

MPDiol Glycol, Unique Properties, ARCO Chemical (1994).

Front and back label from Mennen Speed Stick Clear Deodorant (date unknown, but prior to Sep., 1996).

*Primary Examiner*—S. Mark Clardy
*Assistant Examiner*—Michael A. Williamson
*Attorney, Agent, or Firm*—Stephan P. Williams

[57] ABSTRACT

Soap-based clear cosmetic sticks are disclosed which include an alkali metal salt of a chelating agent into the stick composition to increase the set temperature and the stick hardness and to prevent the formation of precipitates in the composition during aging. A typical composition of the present invention comprises about 40 to 90%, preferably about 50 to 80%, of a polyhydric alcohol, about 5 to 35%, preferably 15 to 30%, water, about 3 to 12%, preferably 4 to 8%, of an alkali metal salt of a $C_{12-22}$, preferably $C_{14-18}$, fatty acid, and about 0.3 to 1.6%, preferably about 0.5 to 1.3% of an alkali metal salt of a chelating agent, preferably a sodium or potassium salt of ethylene diamine tetraacetic acid (EDTA). The composition will also typically contain a cosmetic active ingredient such as a deodorant active. Preferably the composition will contain less than 0.3%, most preferably less than 0.2%, of $C_{20-22}$ soap in order to achieve maximum clarity.

18 Claims, No Drawings

CLEAR COSMETIC STICK COMPOSITION WITH ALKALI CHELATE

BACKGROUND OF THE INVENTION

The present invention relates to clear cosmetic stick compositions, particularly deodorant stick compositions, of improved clarity and stability.

Clear cosmetics sticks comprising a monohydric and/or polyhydric alcohol, a soap gelling agent, and optionally water and one or more emollients are well-known in the art. U.S. Pat. No. 4,226,889 (Yuhas) describes a deodorant stick composition consisting essentially of an aqueous sodium stearate vehicle (100 parts water and 1 to 30 parts sodium stearate) with 0.05 to 0.5% bacteriostat and 0.5 to 10% polyhydroxyl compound. U.S. Pat. No. 4,322,400 (Yuhas) suggests that the setting point of the foregoing composition can be increased by adding 0.5 to 5% sodium chloride. U.S. Pat. No. 4,268,498 (Gedeon) discloses a clear cosmetic stick containing 2 to 5% polyoxyethylene (17–23)-glucose fatty acid ester, 2 to 5% polyoxyethylene (20–60) ether of a long chain alcohol, 24 to 72% PPG(2–5) ether of a long chain alcohol, 5 to 8% soap, 5 to 10% propylene glycol, 5 to 10% lower alkyl ester of a fatty acid, and 2 to 5% water. U.S. Pat. No. 4,617,185 (DiPietro) discloses a deodorant gel stick comprising 6 to 70% polyhydric alcohol, 3 to 10% soap, and 15 to 40% diisopropyl adipate, optionally with 10 to 60% of a PEG/PPG alcohol condensation product such as PPG-14 butanol.

M. de Navarre, The Chemistry and Manufacture of Cosmetics, vol. IV (1975), p. 697, discloses a clear stick formulation comprising 68% propylene glycol, 7% sodium stearate, 10% water, and 15% Pluronic F-127 ($PEO_{98}$-$PPO_{67}$-$PEO_{98}$). U.S. Pat. No. 4,440,742 (Marschner) discloses deodorant sticks comprising 20 to 90% polyhydric alcohol gelled with 2 to 15% soap. Examples 15, 16 and 18 illustrate sticks containing about 44 to 52% propylene glycol or glycerin, 8% sodium stearate, 3 to 4% Procetyl AWS (PPG-5-Ceteth-20), and 35% water. U.S. Pat. No. 4,504,465 (Sampson) discloses a cosmetic gel stick comprising 6 to 70% aliphatic polyhydric alcohol (typically propylene glycol), 3 to 10% soap (typically sodium stearate), and 20 to 80% of a condensation product of the formula $R(OC_3H_6)_a(OC_2H_4)_bOH$ wherein a and b are each 0 to 35 and a+b is 5 to 35 (typically PPG-14 Butanol and PPG-5-Ceteth-20). U.S. Pat. No. 4,759,924 (Luebbe) discloses a clear, cosmetic gel stick containing 40 to 70% aliphatic polyhydric alcohol (typically propylene glycol), 3 to 10% soap (typically sodium stearate), 10 to 40% water, and 1 to 20% of a hydro-alcoholic soluble emollient of the formula $R(OC_3H_6)_a(OC_2H_4)_bOH$ (typically PPG-5-Ceteth-20, PPG-3-Myreth-3, etc.).

U.S. Pat. No. 4,906,454 (Melanson) illustrates in Example 1 a deodorant stick containing 27% propylene glycol, 60% dipropylene glycol, 7% sodium stearate and 4% water. U.S. Pat. No. 5,120,541 (Macaulay) discloses a transparent cosmetic stick which includes 20 to 65% monohydric alcohol, 25.6 to 70% polyhydric alcohol, 3 to 20% soap, 0 to 30% water, and 0.1 to 10% of a soap crystal growth inhibitor such as glycerol monolaurate, sodium ricinoleate, or sodium isostearate.

U.S. Pat. No. 5,128,123 (Brewster) discloses a clear cosmetic stick comprising 10 to 90% polyhydric alcohol, 1 to 40% soap, 1 to 40% alkoxylate copolymer (e.g. Pluronic F-127 or Tetronic 1307), and an amino alcohol clarifying agent (e.g. 2-amino-2-methylpropanol or tetrahydroxypropyl diamine). U.S. Pat. No. 5,221,529 (Tansley) describes a transparent cosmetic stick comprising 20 to 70% glycerol, 3 to 20% soap, 0 to 20% water and 15 to 65% alcohol other than glycerol. U.S. Pat. No. 5,368,848 (Brazinsky) discloses a clear cosmetic stick containing 60 to 90% polyhydric alcohol, 3 to 8% soap, 10 to 20% water, 1 to 7% water soluble emollient having ≧20 PEG groups (e.g. Steareth-100), and 1 to 5% water-dispersible emollient which is a PEG-1 to 6 branched fatty alcohol ether (e.g. Isosteareth-2).

U.S. Pat. No. 5,407,668 (Kellner) discloses a clear deodorant stick comprising 40 to 90% polyhydric alcohol, 10 to 40% water, 1 to 20% soap, 1 to 10% Pentadoxynol-200 and 1 to 20% of a mixture of an alkanolamide (e.g. lauramide DEA) and an alkoxylated alcohol (e.g. Steareth-100 and Isosteareth -2). U.S. Pat. No. 5,424,070 (Kasat) discloses a clear deodorant stick which contains an alkali metal salt of a $C_{12-22}$ fatty acid, with at least some $C_{20-22}$ fatty acid, and a Eumulgin compound, typically PPG-2-Ceteareth-9. Some of the Kasat formulations also include sodium chloride and stearyl alcohol to increase the melting point. U.S. Pat. No. 5,458,880 (Kasat) discloses a clear cosmetic stick comprising an alcohol, water, soap and a sodium salt of a methyl carboxy derivative of ethoxylated lauryl alcohol (e.g. sodium laureth-13 carboxylate).

EP 89,120 (Caserio) discloses a cosmetic gel stick comprising 10 to 50% alkanol (e.g. ethanol), 10 to 50% of a diol chosen from 1,3-, 1,4-, and 2,3-butanediol ,2 to 15% of a soap (e.g. sodium stearate), and 5 to 70% of certain PEG/PPG condensation products (e.g. PPG-14 butyl ether, PPG-5-Ceteth-20).

EP 284,765 (Mortillo) discloses gel sticks comprising sodium stearate and 50 to 81% dipropylene glycol, optionally including water, propylene glycol and deodorant active. The stick may also include up to 0.1% sodium metabisulfite or disodium EDTA. EP 521,579 (Moghe) discloses clear cosmetic gel sticks comprising a polyhydric alcohol, water and sodium stearate and further including sodium chloride and stearyl alcohol to reduce crystal formation.

SUMMARY OF THE INVENTION

It has been discovered that in clear cosmetic sticks comprising a polyhydric alcohol, water and a soap gelling agent, improved clarity and stability can be achieved by incorporating an alkali metal salt of a chelating agent in the composition. In particular, it has been discovered that the inclusion of an alkali metal salt of a chelating agent into the stick composition increases the set temperature and the stick hardness and prevents the formation of precipitates in the composition during aging. This also allows a reduction in the amount of $C_{20-22}$ soap component which would otherwise be required to obtain a sufficiently high set temperature and stick hardness.

A typical composition of the present invention comprises, by weight, about 40 to 90%, preferably about 50 to 80%, of a polyhydric alcohol, about 5 to 35%, preferably 15 to 30%, more preferably 20 to 25%, water, about 3 to 12%, preferably 4 to 8%, of an alkali metal salt of a $C_{12-22}$, preferably $C_{14-18}$, fatty acid, and about 0.3 to 1.6%, preferably about 0.5 to 1.3% of an alkali metal salt of a chelating agent, preferably a sodium or potassium salt of ethylene diamine tetraacetic acid (EDTA). The composition will also typically contain a cosmetic active ingredient such as a deodorant active. Preferably the composition will contain less than 0.3%, most preferably less than 0.2%, of $C_{20-22}$ soap in order to achieve maximum clarity.

DETAILED DESCRIPTION OF THE INVENTION

The present invention is directed to clear cosmetic stick compositions, particularly clear deodorant stick compositions, comprising a polyhydric alcohol, water, a soap gelling agent and an alkali metal salt of a chelating agent. A typical composition of the present invention comprises about 40 to 90%, preferably about 50 to 80%, of a polyhydric alcohol, about 5 to 35%, preferably 15 to 30%, more preferably 20 to 25%, water, about 3 to 12%, preferably 4 to 8%, of an alkali metal salt of a $C_{12-22}$, preferably $C_{14-18}$, fatty acid, and about 0.3 to 1.6%, preferably about 0.5 to 1.3% of an alkali metal salt of a chelating agent, preferably a sodium or potassium salt of ethylene diamine tetraacetic acid (EDTA). In a preferred embodiment the composition will comprise about 20 to 50%, preferably 28 to 46%, more preferably 30 to 40%, of 2-methyl-1,3-propanediol and about 10 to 42%, preferably 18 to 30%, of a polyhydric alcohol other than 2-methyl-1,3-propanediol.

The polyhydric alcohol generally has from 3 to 6 carbon atoms and from 2 to 6 hydroxyl groups and includes, for example, 1,2-propylene glycol, 1,3- propylene glycol, 2-methyl-1,3-propanediol, 1,4-butylene glycol, 1,2-butylene glycol, 1,3-butylene glycol, 2,3-butylene glycol, dipropylene glycol, 2,4- dihydroxy-2-methylpentane, glycerin, sorbitol and the like, and mixtures thereof. Most preferred are 1,2-propylene glycol (commonly referred to simply as propylene glycol), 2-methyl-1,3-propanediol, dipropylene glycol and mixtures thereof. An especially preferred cosmetic stick composition will comprise about 12 to 22% propylene glycol, about 30 to 40% 2-methyl-1,3- propanediol, and about 5 to 10% dipropylene glycol. In addition to the polyhydric alcohol, the stick composition may also optionally include up to about 15% of a lower alkanol, such as ethanol, although the inclusion of such material is not preferred.

The soap gelling agent is an alkali metal salt of a $C_{12}$ to $C_{22}$, preferably $C_{14}$ to $C_{18}$, fatty acid. Preferably the soap is sodium stearate, sodium palmitate or a mixture thereof. Commercial grade sodium stearate typically contains other fatty acid components, particularly sodium palmitate. Some commercial grades of sodium stearate also contain significant amounts of $C_{20-22}$ soap, which may be desirable in some products since the presence of higher carbon chain lengths increases the set temperature and hardness of the stick. However, it has been found that such higher carbon chain lengths are not desirable in clear products since they impart some cloudiness. Accordingly, it is preferred that the soap utilized in compositions of the present invention contain less than about 5%, preferably less than about 4%, $C_{20-22}$ (or higher chain length) fatty component so that the final cosmetic stick composition will contain less than 0.3%, most preferably less than 0.2%, of $C_{20-22}$ soap in order to achieve maximum clarity.

The composition also includes an alkali metal salt, preferably a sodium or potassium salt, of a chelating agent in order to increase the set temperature and hardness of the product to a sufficiently high level and to prevent the formation of precipitates, which reduce clarity, during aging of the composition. By set temperature is meant the temperature at which a small sample (about 10 ml) of the liquid composition begins to solidify. It is preferred that the compositions of the present invention have a set temperature of at least 44° C., more preferably at least 48° C. The selection and amount of polyhydric alcohol, such as 2-methyl-1,3-propanediol, and the amount of alkali metal salt of chelating agent should be adjusted so that the final composition has the desired set temperature.

The alkali metal salts of chelating agents may include salts of citric acid, tartaric acid, salicylic acid, oxalic acid, ethylenediamine-tetraacetic acid (EDTA) such as di-, tri- and tetra-sodium ethylenediamine-tetraacetate ($Na_2EDTA$, $Na_3EDTA$ and $Na_4EDTA$), hydroxyethylethylenediamine-triacetate (HEDTA), diethylenetriamine-pentaacetate (DTPA), nitrilotriacetate (NTA), ethanoldiglycine disodium salt (EDG), diethanolglycine sodium salt (DEG), and 1,3-propylenediamine-tetraacetate (PDTA). A preferred salt is an alkali metal salt of ethylene diamine tetraacetic acid (EDTA). Especially preferred are di-, tri- and tetra-sodium EDTA, with trisodium EDTA being most preferred. These salts are included in the composition in an amount of about 0.3 to 1.6%, preferably about 0.5 to 1.3%.

The alkali metal salt of a chelating agent serves two purposes—it increases the set temperature and it prevents the formation of precipitates in the composition. Without being bound by any theory, it is believed that the alkali metal portion serves to increase the set temperature in a similar manner as the alkali halides known in the art, while the chelate (e.g. EDTA) portion prevents the formation of precipitates by chelating trace metals that can otherwise form insoluble salts with the soap component. These precipitates or crystals generally form as the composition ages and will appear, for example, when the composition is subjected to shelf stability testing at 45° C. for three months or at 60° C. for two months. The compositions of the present invention are free of such precipitates or crystals when subjected to such stability testing.

The cosmetic sticks of the present invention may also include various other ingredients provided that they do not adversely affect the clarity of the stick to any significant extent. For example, the stick may include one or more emollients to improve application aesthetics. It may also include a cosmetic active agent such as a deodorant active agent, a perfume or fragrance, cooling agent, skin conditioning agent, sunscreen agent, etc. Particularly preferred is a deodorant active agent which may include bacteriocides, such as triclosan, and malodor-reducing or malodor-masking agents, such as those disclosed in U.S. Pat. No. 5,213,791 (e.g. aminooxyacetic acid) and WO 91/11988. Deodorant actives are typically incorporated in an amount of about 0.1 to 3%.

The cosmetic stick may also optionally include one or more polyethylene oxide and/or polypropylene oxide condensation products, typically in an amount of about 1 to 10%. These include, for example, copolymers of the formula

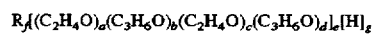

where R is selected from H, a $C_{12-18}$ fatty alkoxide chain, and ethylene diamine; a, b, c and d are integers independently selected from 0 to 200, provided that the sum of a, b, c and d is at least 3;

e is an integer from 1 to 4;

f is an integer from 0 to 1; and g is an integer from 0 to 4.

Such copolymers include the Poloxamers (e.g. the Pluronics and Tetronics from BASF Corp.) as well as the PEG and/or PPG fatty alkoxides such as, for example, PPG-3 Myristyl Ether, Isosteareth-20, PPG-5-Ceteth-20, Steareth-100, Oleth-20, and PPG-14 Butyl Ether. Other polyethoxylated derivatives may also be included such as polyoxyethylene ethers of alkyl substituted phenols, e.g. Nonoxynol-4, Nonoxynol-20 and Pentadoxynol-200. Obviously, the copolymer selected should be one which imparts a desirable aesthetic characteristic to the stick without adversely affecting its clarity.

A "clear" stick, as used herein, is a stick that is visually clear so that, like glass, it allows ready viewing of objects behind it. Preferred clear gel sticks have a turbidity measurement, expressed in Nephelometric Turbidity Units (NTU) of less than about 165 NTU, more preferably less than 100 NTU, and most preferably less than 75 NTU, when measured with a Hellige #965 Direct-Reading Turbidimeter.

Preferred cosmetic stick compositions have a hardness of between about 200 and about 400, more preferably between about 225 and about 350, when measured on a TA-XT2 Texture Analyzer (Stable Micro System, Haste Hill, England). These hardness measurements correlate to the grams of force required for the standard arrowhead-type penetration needle to penetrate the stick a distance of 5 mm at 1 mm per second.

The invention may be further illustrated by the following examples in which the parts and percentages are by weight.

EXAMPLES

Deodorant sticks having the compositions shown in the following Table were prepared by combining the ingredients (except fragrance, which is added during cooling) at elevated temperature (typically 80° to 85° C.), pouring into stick-form molds, then cooling under refrigeration at 5° to 15° C. until set. The set temperature for each composition is also given. Each of the sticks was of exceptional clarity.

| Ingredient | Ex. 1 | Ex. 2 | Ex. 3 | Ex. 4 | Ex. 5 | Ex. 6 | Ex. 7 | Ex. 8 | Ex.9 |
|---|---|---|---|---|---|---|---|---|---|
| 2-methyl-1,3-propanediol | 34.7 | 34.7 | 34.7 | 34.7 | 34.7 | 34.7 | | | |
| propylene glycol | 17.2 | 16.1 | 17.5 | 15.4 | 14.5 | 13.2 | 15.5 | 15.5 | 15.5 |
| dipropylene glycol | 7.5 | 7.5 | 7.5 | 7.5 | 7.5 | 7.5 | 42.2 | 42.2 | 42.2 |
| water | 21.0 | 23.0 | 23.0 | 23.0 | 25.0 | 25.0 | 24.0 | 23.3 | 23.0 |
| sodium stearate[1] | 5.4 | 5.4 | 5.4 | 5.4 | 5.4 | 5.4 | 5.4 | 5.4 | 5.4 |
| PPG-3 Myristyl Ether | 2.7 | 2.7 | 2.7 | 2.7 | 2.7 | 2.7 | 2.7 | 2.7 | 2.7 |
| Isosteareth-20 | 6.5 | 6.5 | 6.5 | 6.5 | 6.5 | 6.5 | 6.5 | 6.5 | 6.5 |
| diisopropyl sebacate | 1.0 | 1.0 | 1.0 | 1.0 | 1.0 | 1.0 | 1.0 | 1.0 | 1.0 |
| trisodium EDTA | 1.6 | 0.7 | 1.0 | 1.3 | 0.3 | 1.6 | 0.3 | 1.0 | 1.3 |
| triclosan | 0.3 | 0.3 | 0.3 | 0.3 | 0.3 | 0.3 | 0.3 | 0.3 | 0.3 |
| fragrance/preservative | q.s | q.s | q.s | q.s | q.s | q.s | q.s | q.s | q.s |
| set temperature (°C.) | 54 | 50 | 50 | 50 | 50 | 52 | | | |

[1] A blend of 5.0 parts OP-100 and 0.4 parts OP-200 from RTD Chemicals (total $C_{20-22}$ < 0.2 parts)

What is claimed is:

1. A clear cosmetic stick composition comprising, by weight, about 40 to 90% of a polyhydric alcohol, about 5 to 35% water, about 3 to 12% of an alkali metal salt of a $C_{12-22}$ fatty acid, and about 0.3 to 1.6% of an alkali metal salt of a chelating agent, wherein said composition contains less than 0.3% of an alkali metal salt of a $C_{20-22}$ fatty acid.

2. The composition of claim 1 wherein the polyhydric alcohol has from 3 to 6 carbon atoms and from 2 to 6 hydroxyl groups.

3. The composition of claim 2 comprising about 50 to 80% of a polyhydric alcohol and about 15 to 30% water.

4. The composition of claim 3 wherein the polyhydric alcohol is selected from the group consisting of propylene glycol, 2-methyl-1,3-propanediol, dipropylene glycol and mixtures of at least two of these polyhydric alcohols.

5. The composition of claim 4 comprising about 4 to 8% of an alkali metal salt of a $C_{14-18}$ fatty acid.

6. The composition of claim 4 comprising about 4 to 8% of an alkali metal salt of a $C_{14-18}$ fatty acid.

7. The composition of claim 1, 2, 3, 4, 5 or 6 wherein the alkali metal salt of a chelating agent comprises di-, tri- or tetra-sodium ethylenediaminetetraacetate.

8. The composition of claim 7 having a set temperature of at least 48° C. and a turbidity of less than 100 NTU.

9. The composition of claim 8 additionally comprising a deodorant active.

10. The composition of claim 1 wherein said composition contains less than 0.2% of an alkali metal salt of a $C_{20-22}$ fatty acid.

11. The composition of claim 1 having a set temperature of at least 48° C. and a turbidity of less than 100 NTU.

12. The composition of claim 10 or 11 wherein the polyhydric alcohol is selected from the group consisting of propylene glycol, 2-methyl-1,3-propanediol, dipropylene glycol and mixtures of at least two of these polyhydric alcohols.

13. The composition of claim 12 wherein the alkali metal salt of a chelating agent comprises di-, tri- or tetra-sodium ethylenediaminetetraacetate.

14. The composition of claim 4 comprising about 12 to 22% propylene glycol, about 30 to 40% 2-methyl-1,3-propanediol, and about 5 to 10% dipropylene glycol.

15. The composition of claim 14 comprising about 0.5 to 1.3% of di-, tri- or tetra-sodium ethylenediaminetetraacetate.

16. The composition of claim 15 comprising about 20 to 25% water.

17. The composition of claim 1 additionally comprising a deodorant active.

18. The composition of claim 1 additionally comprising a copolymer of the formula

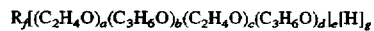

where R is selected from H, a $C_{12-18}$ fatty alkoxide chain, and ethylene diamine;

a, b, c and d are integers independently selected from 0 to 200, provided that the sum of a, b, c and d is at least 3;

e is an integer from 1 to 4;

f is an integer from 0 to 1; and g is an integer from 0 to 4.

* * * * *

UNITED STATES PATENT AND TRADEMARK OFFICE
CERTIFICATE OF CORRECTION

PATENT NO. : 5,798,094
DATED : August 25, 1998
INVENTOR(S) : Tuan M. Vu, et al

It is certified that error appears in the above-identified patent and that said Letters Patent is hereby corrected as shown below:

In Claim 5, at col. 5, line 60 change "$C_{14-18}$" to --$C_{12-22}$--.

Signed and Sealed this

Eighth Day of December, 1998

*Attest:*

BRUCE LEHMAN

*Attesting Officer*       Commissioner of Patents and Trademarks